(12) United States Patent
Singh et al.

(10) Patent No.: US 7,130,061 B2
(45) Date of Patent: Oct. 31, 2006

(54) SYSTEM AND METHOD FOR MONITORING PROPERTIES OF A MEDIUM BY FIBER OPTICS

(75) Inventors: Nahar Singh, Chandigarh (IN); Subhash Chander Jain, Chandigarh (IN); Anil Kumar Aggarwal, Chandigarh (IN); Ram Prakash Bajpai, Chandigarh (IN)

(73) Assignee: Council of Scientific and Industrial Research, New Delhi (IN)

( * ) Notice: Subject to any disclaimer, the term of this patent is extended or adjusted under 35 U.S.C. 154(b) by 386 days.

(21) Appl. No.: 10/813,425

(22) Filed: Mar. 31, 2004

(65) Prior Publication Data

US 2004/0262550 A1 Dec. 30, 2004

Related U.S. Application Data

(60) Provisional application No. 60/458,448, filed on Mar. 31, 2003.

(51) Int. Cl.
*G01B 11/28* (2006.01)

(52) U.S. Cl. .................................................. 356/630
(58) Field of Classification Search ................. 356/630
See application file for complete search history.

(56) References Cited

U.S. PATENT DOCUMENTS

| 5,373,487 | A | * | 12/1994 | Crawford et al. | 367/149 |
| 6,785,010 | B1 | * | 8/2004 | Kimba et al. | 356/630 |
| 6,897,964 | B1 | * | 5/2005 | Takahashi et al. | 356/503 |
| 2003/0160973 | A1 | * | 8/2003 | Nakayama et al. | 356/630 |

* cited by examiner

*Primary Examiner*—Gregory J. Toatley, Jr.
*Assistant Examiner*—Isiaka O. Akanbi
(74) *Attorney, Agent, or Firm*—Nixon Peabody LLP; Donald R. Studebaker

(57) ABSTRACT

The present invention relates to a system for monitoring properties of a medium by fiber optics. The present invention particularly relates to a system of fiber optics for monitoring layer thickness of immiscible liquids for industrial applications and a method thereof.

23 Claims, 1 Drawing Sheet

Schematic of Fiber Optic Technique for Monitoring Layer Thickness of Immiscible Liquids

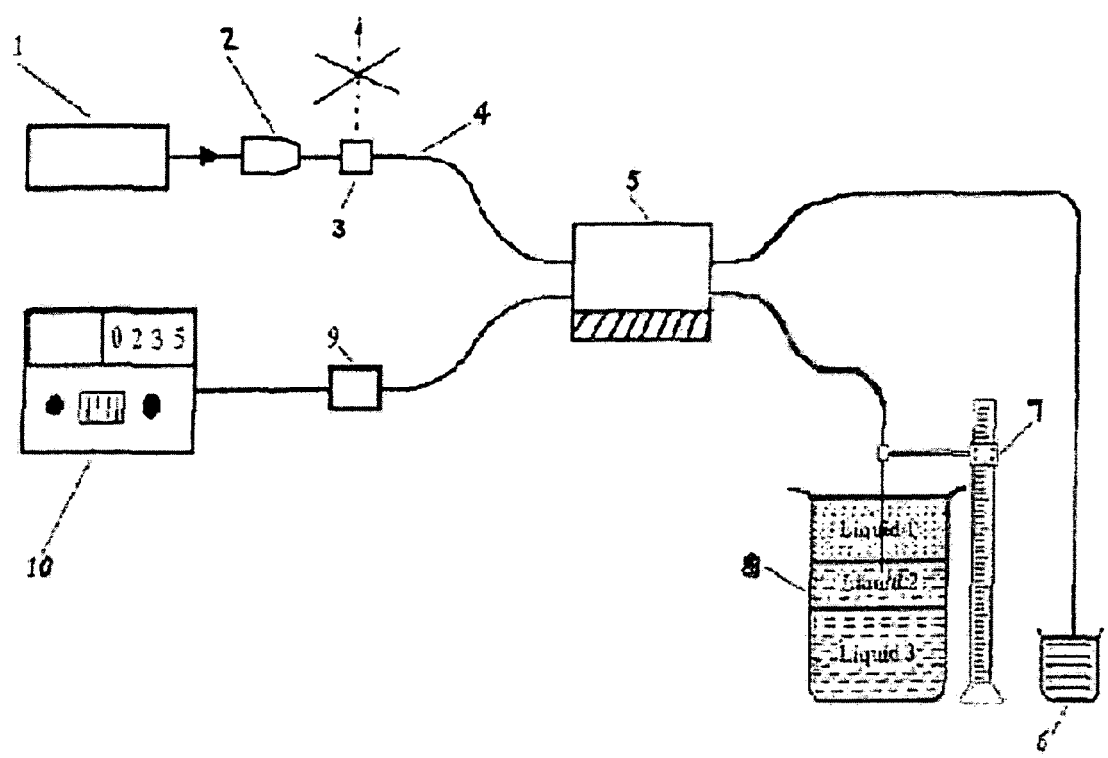
Figure 1. Schematic of Fiber Optic Technique for Monitoring Layer Thickness of Immiscible Liquids

SYSTEM AND METHOD FOR MONITORING PROPERTIES OF A MEDIUM BY FIBER OPTICS

FIELD OF THE INVENTION

The present invention relates to a system for monitoring properties of a medium by fiber optics. More particularly, the present invention particularly relates to a system of fiber optics for monitoring layer thickness of immiscible liquids for industrial applications and a method thereof.

BACKGROUND ART AND PRIOR ART REFERENCE

The layer thickness of immiscible liquids is being measured by manual techniques which involve either knowing the layer thickness from the known volume of liquids and the diameter of the container or visually reading the layer thickness using a scale or graduations provided on the container wall. It may be mentioned that the optical techniques based on using optical fibers and lasers for this application are mostly under research and development stage at present.

The conventional techniques are based on human observation and their accuracy shall depend on the person to person while the present technique is based on the principle of Fresnel reflection, which is quite sensitive to changes in refractive index of the medium making contact with the fiber end face. The layer thickness monitoring of immiscible liquids is a very natural and novel application of this technique because, every liquid is identified by its optical parameter which is refractive index. In this technique, the changes in refractive index are read photometrically in term of optical power variations using sensitive photodetectors. This technique based on instrumentation besides being more accurate is also more reliable, efficient and fast as compared to those based on direct human observation. In addition, this technique is more suitable for an industrial application where speed, efficiency and automatic remote monitoring are the highly desirable features.

This technique is useful for remote layer thickness monitoring of immiscible liquids in an industrial process. It is particularly useful for monitoring layer thickness of immiscible liquids in hostile, inflammable, corrosive and electromagnetically noisy environments as encountered in petrochemical and process control industry.

The novelty aspect of the present invention is the application of the principle of Fresnel reflection in optical fibers that depends on the difference of refractive indices of the fiber core and the surrounding medium. This technique overcomes the above-mentioned problems effectively and provides the added advantage of remote and in-situ monitoring. There is no electrical signal being guided and it is only the light signal which is transmitted through optical fibers and is unaffected by the presence of electrical signals.

A research paper based on this technique for measurement of temperature, contamination and layer thickness of immiscible liquids has been published in Experimental Techniques (USA), 36–38, March/April 2002 printed by the Society for Experimental Mechanics (SEM), Inc., 7 School Street, Bethel, Conn. 06801, (203) 790–6373, www.sem.org.

OBJECTS OF THE INVENTION

The main object of the present invention is to provide an optic fiber system for reliable, durable, cost-effective and in-situ layer thickness monitoring of properties of a medium.

An object of the present invention is to provide a system for measuring layer thickness of immiscible liquids.

Another object of the present invention is to provide a method for measuring the layer thickness and physical properties of a medium.

SUMMARY OF THE INVENTION

The present invention relates to a system for monitoring properties of a medium by fiber optics. The present invention particularly relates to a system of fiber optics for monitoring layer thickness of immiscible liquids for industrial applications and a method thereof.

BRIEF DESCRIPTION OF DRAWINGS

FIG. 1: Schematic Diagram of Fiber Optic System for monitoring layer thickness of immiscible liquids, wherein
1. He—Ne Laser
2. Microscope objective
3. Precision fiber positioner/holder
4. Optical fiber
5. 3 dB fiber optic bitaper fused directional coupler
6. refractive index matching liquid
7. micro positioning vertical movement stage
8. column of immiscible liquids
9. Si PIN photo detector
10. High sensitivity optical power meter

DETAILED DESCRIPTION OF THE INVENTION

Accordingly, the present invention provides a fiber optic technique for monitoring layer thickness of immiscible liquids, said system comprising:
  a) a light source emitting optical signal;
  b) an optical signal distributing means connected to the light source and distribution the optical signal received from the light source;
  c) a position measuring means for holding one of the output of the optical signal distribution means;
  d) a refractive index matching liquid, immersed in it second output of the optical signal distribution means; and
  e) an optical powermeter connected to the optical signal distribution means for measuring the optical signal reflected from the medium.

In another embodiment of the present invention, the light source is selected from the group consisting of He—Ne laser.

In another embodiment of the present invention, the optical signal distribution means is a fiber optic directional coupler.

In another embodiment of the present invention, the light source is connected to the optical signal distribution means through a microscope objective and a precision fiber positioner.

In another embodiment of the present invention, wherein the position measuring means is a micro-positioning vertical movement stage.

In another embodiment of the present invention, wherein the optical power meter is connected to the optical signal distribution means through a photo detector.

In another embodiment of the present invention, the system is based on Fresnel reflection.

In another embodiment of the present invention, wherein mediums are immiscible liquids.

In another embodiment of the present invention, wherein He—Ne laser serves as a light source for feeding the input port of the fiber optic coupler used in the technique.

In another embodiment of the present invention, wherein Microscope objective is used for efficient coupling light into the optical fiber.

In another embodiment of the present invention, wherein Precision fiber positional/holder is used for alignment of the fiber with respect to the microscope objective for efficient launching light into the fiber.

In another embodiment of the present invention, wherein Optical fiber is a single mode optical fiber used for realizing Fresnel Reflection for various measurements.

In another embodiment of the present invention, wherein 3 dB fiber optic bitaper fused directional coupler: This coupler divides the input laser beam into two equal parts and directs them to the two output ports.

In another embodiment of the present invention, wherein the free (redundant) fiber end of the second output port is dipped in the refractive index matching liquid to avoid Fresnel reflection which will interfere with the measurements.

In another embodiment of the present invention, wherein Micropositioning vertical movement stage carries the sensing fiber for its vertical movement in the column of immiscible liquids and provides measurement of the layer thickness.

In another embodiment of the present invention, wherein Column of immiscible liquids is a column of immiscible liquids contained in a container for testing purposes.

In another embodiment of the present invention, wherein Si PIN Photodetector is the silicon PIN photodetector which detects the Fresnel reflected optical signal as per the value of refractive index of the medium (liquid) surrounding the sensing fiber end face.

In another embodiment of the present invention, wherein High sensitivity optical power meter is a high sensitivity optical power meter to display the detected Fresnel reflection signal.

In another embodiment of the present invention, the optical signal propagation is secure and without any cross talk or interference problems.

In another embodiment of the present invention, the optical signal is unaffected by the presence of electrical signals.

In another embodiment of the present invention, all the inter-connections are through optical fibers.

In another embodiment of the present invention, an alarm or actuator is coupled to the powermeter/photodetector to provide signal if the powermeter value has exceeded safe predetermined operational value.

In another embodiment of the present invention, the optical fibers are made of dielectric material that is non-corrosive, durable and immune to any Electro Magnetic Interference (EMI) and RFI.

In another embodiment of the present invention, the system exhibits an accuracy of at least 99%.

The present invention also provides a method for measuring the thickness of the mediums, said method comprising:
a) immersing first output of the optical signal distribution means in the medium;
b) immersing the second output of the optical signal distribution means in the refractive index matching liquid;
c) emitting light from the light source to the optical signal distribution means;
d) monitoring the position of position measuring means; and
e) detecting the reflected signal using the photo detector and optical powermeter reflected from the medium.

In another embodiment of the present invention, position of the position measuring means is monitored before the immersion of first output in the medium.

In another embodiment of the present invention, the reflected signal is detected in the optical powermeter.

In another embodiment of the present invention, the reflected signal is dependent upon the medium surrounding the fiber core of the first output.

In another embodiment of the present invention, the change in the reflected signal indicates change in the medium.

In another embodiment of the present invention, the position difference of the position measuring means when there is a difference in the reflected signal detected in the powermeter indicates the thickness of the medium.

In another embodiment of the present invention, the reflected optical signal is Fresnel reflected signal.

In another embodiment of the present invention, mediums are immiscible liquids.

In another embodiment of the present invention, the method exhibits an accuracy of at least 99%.

In another embodiment of the present invention, light is launched from a He—Ne laser into one port of the 3 dB fiber optic directional coupler using a microscope objective & a 3-axis fiber positioner and monitoring the Fresnel reflected signal by means of a photodetector/optical power meter.

In another embodiment of the present invention, Fresnel reflection taking place at the output port depends on the refractive index of the medium surrounding the fiber core.

In another embodiment of the present invention, at one of the output ports, the fiber end face is mounted on a vertically moving micropositioning stage while the fiber endface at the other output port is immersed in an index matching liquid to reduce Fresnel reflection.

In another embodiment of the present invention, the Fresnel reflected signal is detected at the other port by means of a Si PIN photodetector and optical powermeter.

In another embodiment of the present invention, the fiber endface mounted on the stage vertically traverses the column of immiscible liquids and identifies start of the layer of a different liquid by sudden change in the level of Fresnel reflected signal.

In another embodiment of the present invention, the distance moved by the stage/fiber endface between the detected two different levels of Fresnel reflected signals, indicates the layer thickness of the liquid column traversed.

In another embodiment of the present invention, layer thickness of different immiscible liquids contained in a column is determined by this technique.

In another embodiment of the present invention a suitable fiber optic technique based on Fresnel reflection has been identified, developed and implemented for the particular application of monitoring the layer thickness of immiscible liquids. The technique can be easily automated for in situ and remote monitoring of the layer thickness.

In another embodiment of the present invention, a 3 dB fiber optic coupler has been employed which consists of optical fibers made of silica, a highly durable material being non-conductve and noninductive in nature.

In another embodiment of the present invention, the sensing signal is in the form of intensity modulated light guided by the fiber.

In another embodiment of the present invention, the signal propagation is secure without any crosstalk or interference problems.

In another embodiment of the present invention, the fiber optic technique based on Fresnel reflection comprises of launching light from a He—Ne laser into one port of the 3 dB fiber optic directional coupler by means of a microscope objective & a 3-axis fiber positioner and monitoring the Fresnel reflected signal by means of a photodetector/optical powermeter.

In another embodiment of the present invention, Fresnel reflection taking place at the output port depends on the refractive index of the medium surrounding the fiber core.

In another embodiment of the present invention, at one of the output ports, the fiber endface is mounted onto a vertically moving micropositioning stage while the fiber endface at the other output port is immersed in an index matching liquid.

In another embodiment of the present invention, the Fresnel reflected signal is detected by means of a Si PIN photodetector and optical powermeter at the other port.

In another embodiment of the present invention, the fiber endface mounted on the stage vertically traverses the column of immiscible liquids and identifies the start of the layer of a different liquid by sudden change in the level of Fresnel reflected signal.

In another embodiment of the present invention, the distance moved by the stage/fiber endface between the two different levels of Fresnel reflected signals detected, indicates the layer thickness of the liquid column traversed.

In another embodiment of the present invention, layer thickness of different immiscible liquids contained in a column is determined by this technique.

In another embodiment of the present invention, when the probing fiber end just touches the top layer of first liquid, a signal corresponding to the Fresnel reflection occurred is detected and the zero position of the stage is noted.

In another embodiment of the present invention, the fiber end is then made to traverse the first liquid and as soon as the layer of the second liquid starts, there is a sudden change in the Fresnel reflected signal and the position of the stage at this point is again noted.

In another embodiment of the present invention, the difference between these two positions of the stage gives the layer thickness of the first liquid.

In another embodiment of the present invention, the layer thickness of other immiscible liquids contained in the column is determined in a similar way using this technique.

In another embodiment of the present invention, the technique facilitates monitoring of layer thickness of immiscible liquids employing the principle of Fresnel reflection occurring at an output port of a fiber optic directional coupler as the medium surrounding the fiber core is varied.

In another embodiment of the present invention, this process of Fresnel reflection basically involves intensity modulation of the signal and is unaffected by a hostile and electrically noisy environment whereas the prior art is not immune to hostile/hazardous/corrosive environments encountered in petrochemical and other industries. This is so because optical fibers are made from dielectric materials and therefore, they are both non-inductive and non-conductive in nature, thereby bringing immunity to EMI/RFI. Also the basic raw material, optical glass from which fibers are made is quite durable and effectively withstands harsh and corrosive environments encountered in various application areas.

In another embodiment of the present invention, The optical fibers are made of dielectric material, which is non-conductive, non-inductive, non-corrosive, durable and immune to any EMI/RFI effects.

In another embodiment of the present invention, the level of Fresnel reflected signal suddenly changes as the fiber end face traversing a liquid touches another liquid. The vertical distance moved by the stage between the start of a liquid layer and then start of another liquid indicates the layer thickness of the first liquid.

In another embodiment of the present invention, the technique thus facilitates determination of the layer thickness of immiscible liquids. It is a simple and useful technique, which can be employed in harsh environments particularly encountered in petrochemical industries for in-situ monitoring of layer thickness of immiscible liquids and liquid levels in storage tanks.

In another embodiment of the present invention, the present invention is capable of sensing different physical and chemical parameters such as pressure, electric field, magnetic field etc by using suitable cap materials. The present system also comprises a collimator lens on the face of sensing fiber end, to facilitate collimated beam from the fiber thereby increasing the reflected optical power.

This technique could be beneficially used for monitoring layer thickness of immiscible liquids for various scientific, industrial and medical applications. This could also be used for remote level monitoring of tanks containing chemical liquids in an industry. An alarm can be generated as soon as a specified level of the liquid is attained or the filling system is shut by an actuator signal. The layer thickness monitoring can be carried out remotely by extending the length of soptical fiber arms of the coupler. It can be quite a durable and cost-effective technique and the process monitoring operation can be made automatic.

This technique has been implemented in the Laboratory by mixing known volumes of different combinations of immiscible liquids (olive oil and water; $CCl_4$ and water; $CCl_4$ and acetone; olive oil and glycerol) in a small graduated jar. The layer thickness of the individual liquids was calculated from respective volumes added into the jar as well as measured by lowering the sensing fiber end into the stack of liquids contained in the jar by means of the micro-positioning stage. There is instantaneous change in the reflected optical power as soon as one liquid is replaced by another liquid thereby indicating start of a new layer and the technique provides a convenient means of determining the layer thickness of a liquid. A good correlation was observed between the calculated and measured values of layer thickness of immiscible liquids for the different liquids used, and the technique has exhibited a typical variation of 0.5–1% in the layer thickness measurement.

The present invention provides development and implementation of a fiber optic system for monitoring layer thickness of immiscible liquids. This technique makes use of a 3 dB fiber optic directional coupler and works on the principle of Fresnel reflection occurring in a fiber core at one of the coupler output port Accordingly, the amount of light thus reflected depends on the difference of refractive indices of the core material and the surrounding medium and provides a simple means for measurement of refractive index of liquids. The technique can facilitate remote/in-situ monitoring of layer thickness of immiscible liquids and be made automatic. It offers several advantages over the conventional methods.

A typical comparison data shows the accuracy of the present invention and the example given should not be construed to limit the scope of the invention:

Diameter of the glass container: 2.54 cm
Area of cross section of the container: 5.064 cm$^2$

| Sr. No. | Volume of liquid used | Calculated Layer Thickness | Measured Layer thickness | % Variation |
|---|---|---|---|---|
| 1 | 5 cc Water | 9.88 mm | 9.95 mm | 0.70 |
| 2 | 8 cc Glycerol | 15.81 mm | 15.95 | 0.88 |
| 3 | 10 cc Olive oil | 19.76 mm | 19.65 | 0.55 |

Advantages of the Present Invention
1. It can work for process industry applications where the environment is hostile- and electrically noisy.
2. It can monitor remotely layer thickness of immiscible liquids and the process can be made automatic.
3. It can monitor level of liquids in tanks specially filled with corrosive and explosive hazardous chemicals/liquids and give an alarm.
4. A long column of several immiscible liquids can be monitored employing a long optical fiber, which is not at all a problem as optical fibers are lightweight and flexible entity.
5. The technique could also be used for monitoring temperature and contamination/purity for various industrial and other applications,
6. A simple, low cost and durable technique.

We claim:

1. A fiber optic system for monitoring properties of mediums, said system comprising:
   a) a light source emitting optical signal;
   b) an optical signal distribution means connected to the light source and distribution the optical signal received from the light source;
   c) a position measuring means for holding one of the output of the optical signal distribution means;
   d) a refractive index matching liquid, immersed in it second output of the optical signal distribution means; and
   e) an optical powermeter connected to the optical signal distribution means for measuring the optical signal reflected from the medium.

2. The system as claimed in claim 1, wherein the light source for feeding the input port of the optical signal distribution means is selected from the group consisting of He—Ne laser.

3. The system as claimed in claim 1, wherein the optical signal distribution means is a fiber optic bi-directional coupler.

4. The system as claimed in claim 1, wherein the light source is connected to the optical signal distribution means through a microscope objective, providing efficient coupling light into the optical fiber, and a precision fiber positioner, providing alignment of the fiber with respect to the microscope objective for efficient launching light into the fiber.

5. The system as claimed in claim 1, wherein the freefiber end of the second output port is dipped in the refractive index matching liquid to avoid Fresnel reflection which will interfere with the measurements.

6. The system as claimed in claim 1, wherein the position measuring means is a micro-positioning vertical movement stage.

7. The system as claimed in claim 1, wherein the optical power meter is connected to the optical signal distribution means through a photo detector.

8. The system as claimed in claim 1, wherein the system is based on Fresnel reflection.

9. The system as claimed in claim 1, wherein mediums are immiscible liquids.

10. The device as claimed in claim 1, wherein the optical signal propagation is secure and without any cross talk or interference problems.

11. The system as claimed in claim 1, wherein the optical signal is unaffected by the presence of electrical signals.

12. The system as claimed in claim 1, wherein all the connections are through optical fibers.

13. The system as claimed in claim 12, wherein the optical fibers are made of dielectric material that is non-corrosive, durable and immune to any Electro Magnetic Interference (EMI) and RFI.

14. The system as claimed in claim 13, wherein the system exhibits an accuracy of at least 99%.

15. A method for measuring the thickness of the mediums, said method comprising:
   f) immersing first output of the optical signal distribution means in the medium;
   g) immersing the second output of the optical signal distribution means in the refractive index matching liquid;
   h) emitting light from the light source to the optical signal distribution means;
   i) monitoring the position of position measuring means; and
   j) detecting the reflected signal using the photo detector and optical powermeter reflected from the medium.

16. The method as claimed in claim 10, wherein position of the position measuring means is monitored before the immersion of first output in the medium.

17. The method as claimed in claim 10, wherein the reflected signal is detected in the optical powermeter.

18. The method as claimed in claim 10, wherein the reflected signal is dependent upon the medium surrounding the fiber core of the first output.

19. The method as claimed in claim 10, wherein the change in the reflected signal indicates change in the medium.

20. The method as claimed in claim 10, wherein the position difference of the position measuring means when there is a difference in the reflected signal detected in the powermeter indicates the thickness of the medium.

21. The method as claimed in claim 10, wherein the reflected optical signal is Fresnel reflected signal.

22. The method as claimed in claim 1, wherein mediums are immiscible liquids.

23. The method as claimed in claim 1, wherein the method exhibits an accuracy of at least 99%.

* * * * *